United States Patent

Summers et al.

[11] Patent Number: 5,439,022
[45] Date of Patent: Aug. 8, 1995

[54] LAVAGE VALVE

[76] Inventors: Daniel A. Summers, 5701 Klondike, NE.; Howard Levy, 8708 Caminito Dr. NE., both of, Albuquerque, N. Mex. 87111

[21] Appl. No.: 195,926

[22] Filed: Feb. 14, 1994

[51] Int. Cl.⁶ .............................................. F16K 11/02
[52] U.S. Cl. ..................... 137/102; 137/107; 251/65
[58] Field of Search .................... 137/102, 107; 251/65

[56] References Cited

U.S. PATENT DOCUMENTS

| | | | |
|---|---|---|---|
| 657,440 | 9/1900 | McCaw . | |
| 1,091,463 | 3/1914 | Vincent | 137/107 |
| 1,222,316 | 4/1917 | Matthewman | 137/107 |
| 2,567,391 | 9/1951 | Mead | 251/118 |
| 2,721,572 | 10/1955 | MacDonnell | 137/102 |
| 2,764,174 | 9/1956 | Wilson | 137/102 |
| 3,027,907 | 4/1962 | Lee | 137/107 |
| 3,515,163 | 6/1970 | Freeman | 137/102 |
| 3,516,443 | 6/1970 | Hughes | 137/102 X |
| 3,877,616 | 4/1975 | Stevens | 222/321 |
| 3,957,052 | 5/1976 | Topham | 128/278 |
| 4,051,852 | 10/1977 | Villari | 128/278 |
| 4,240,433 | 12/1980 | Bordow | 128/347 |
| 4,246,932 | 1/1981 | Raines | 137/512 |
| 4,447,235 | 5/1984 | Clarke | 604/169 |
| 4,592,382 | 6/1986 | Rubin et al. | 137/218 |
| 4,729,401 | 3/1988 | Raines | 137/512 |
| 4,784,156 | 11/1988 | Garg | 128/753 |
| 4,832,044 | 5/1989 | Garg | 128/753 |
| 4,840,184 | 6/1989 | Garg | 128/753 |
| 4,844,087 | 7/1989 | Garg | 128/753 |

*Primary Examiner*—Stephen M. Hepperle
*Attorney, Agent, or Firm*—Deborah A. Peacock; Donovan F. Duggan; Jeffrey D. Myers

[57] ABSTRACT

Disclosed is a lavage valve apparatus and a method of using the valve. The valve comprises a valve body having three apertures and a bypass passageway. A movable valve member with truncated end portions moves linearly within the valve body by means of hydraulic pressure or mechanical (or magnetic) bias. Application of hydraulic pressure via a syringe pumps irrigation fluid through the valve into the patient. Termination of hydraulic pressure allows mechanical reseating of the movable valve member and vacuum withdrawal of the fluid.

13 Claims, 3 Drawing Sheets

LAVAGE VALVE

CROSS-REFERENCE TO RELATED APPLICATIONS

A related application is being filed concurrently herewith, entitled *Paracentesis Valve* to Daniel A. Summers, Attorney Docket No. 41312-9303, and the specification thereof is incorporated herein by reference.

BACKGROUND OF THE INVENTION

1. Field of the Invention (Technical Field)

The invention relates to a lavage valve operable solely by mechanical (including magnetic) and hydraulic force; and a method for using such valve.

2. Background Art

Previously, the medical procedure for irrigation or lavage of organs, joints or cavities required manual manipulation of a three-way valve. Together, with the requisite needle, syringe, vacuum source and tubing, the three-way valve would first be manually manipulated to direct the laving fluid into the patient; then again manually manipulated to allow expulsion of the fluid from the patient. The disadvantages of this procedure include patient discomfort, improper valve manipulation, valve jamming (as with gloves, etc.) and the risk of torn gloves and subsequent infection.

The following U.S. patents illustrate the manual valves of the prior art: U.S. Pat. No. 4,844,087 to Garg, entitled *First Method for Using Cannula Including a Valve Structure and Associated Investment Element;* U.S. Pat. No. 4,447,235 to Clarke, entitled *Thoracentesis Device;* U.S. Pat. No. 4,784,156 to Garg, entitled *Cannula Including a Valve Structure and Associated Instrument Elements and Method for Using Same;* U.S. Pat. No. 4,840,184 to Garg, entitled *Second Method for Using Cannula Including a Valve Structure and Associated Instrument Elements;* and U.S. Pat. No. 4,832,044 to Garg, entitled *Cannula including a Valve Structure and Associated Instrument Elements.*

U.S. Pat. No. 3,957,052, to Topham, entitled *Pumping-Syringe,* discloses a T-passageway valve configuration for withdrawing and pumping fluids. Ball check valves are used. Similarly, U.S. Pat. No. 4,051,852, to Villari, entitled *Aspirating Device,* discloses ball, flap and cylindrical check valve member embodiments for withdrawing body fluids and thereafter pumping them into suitable collection bags. U.S. Pat. No. 657,440 to McCaw, entitled *Aspirator,* discloses similar structure.

U.S. Pat. No. 3,515,163 to Freeman, entitled *Respiratory Apparatus* does disclose a respiratory valve with a sliding valve member. The sliding valve member, however, is magnetically biased, and flow occurs through centrally located orifices in the sliding valve member. U.S. Pat. No. 3,877,616, to Stevens, entitled *Pump With Unitary Valve Member,* discloses a reciprocating valve member with upper and lower resilient check valves. U.S. Pat. No. 4,592,382, to Rubin, et al., entitled *Anti-Siphon Nozzle,* discloses an unbiased slidable valve member.

U.S. Pat. No. 4,246,932, to Raines, entitled *Multiple Additive Valve Assembly;* and U.S. Pat. No. 4,729,401, to Raines, entitled *Aspiration Assembly Having Dual Co-Axial Check Valves,* both disclose pumping devices for medical fluids employing resilient disk check valves. U.S. Pat. No. 2,567,391 to Mead, entitled *Exhaust Valve Structure* also discloses a resilient valve member.

It is seen that none of the above references disclose a biased slidable valve member operable solely by mechanical (or magnetic) and hydraulic force to first direct laving or irrigating fluid into the patient, then automatically withdrawing such fluid.

SUMMARY OF THE INVENTION (DISCLOSURE OF THE INVENTION)

In accordance with the present invention there is provided a valve apparatus. The valve apparatus comprises a valve body. The valve body comprises first, second and third orifices and a bypass passageway. A valve member comprising first and second end portions is movable within the valve body. Structure is provided for biasing the valve member.

The valve member comprises a cylindrical center portion, and the first and second end portion comprise first and second truncated cone end portions. The valve body comprises a hollow central portion complementary in configuration to the valve member. The structure for biasing the valve member comprises structure for biasing the valve member into occluding the first orifice and bypass passageway while opening the second and third orifices.

The biasing structure may comprise a helical spring, an annular spring or magnetic structure. Applying pressure to the first end portion opens the first orifice and bypass passageway while occluding the third orifice. The structure for applying pressure comprises structure for applying hydraulic pressure, thereby directing fluid flow through the first and second orifices and the bypass passageway. The bypass passageway comprises an aperture and a pressure relief valve or a pressure gauge is disposed in the aperture.

In accordance with the present invention there is provided a method for using a valve comprising the steps of providing a valve body comprising first, second and third orifices and a bypass passageway; providing a valve member comprising first and second end portions; and movable in the valve body; and biasing the valve member. The step of biasing the valve member further comprises the steps of occluding the first orifice and bypass passageway while opening the second and third orifices. The step of applying pressure to the first end portion opens the first orifice and bypass passageway while occluding the second and third orifices. The step of applying pressure further comprises the step of applying hydraulic pressure and thereby directing fluid flow through the first and second orifices and the bypass passageway.

A primary object of the present invention is the provision of a hydraulically and mechanically operated lavage valve.

Another object of the invention is the provision of a lavage valve which automatically reverses fluid flow.

Yet another object of the invention is the provision of a lavage valve which reduces patient discomfort and the possibility of operator error.

Still another object of the invention is the provision of an improved method for lavage procedure.

An advantage of the present invention is the elimination of manual manipulation of a three-way valve.

Another advantage of the present invention is the lessening of time, effort and fatigue in performing a lavage procedure.

Still another advantage of the present invention is the provision of a safe and efficient lavage method.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

Figure 1:
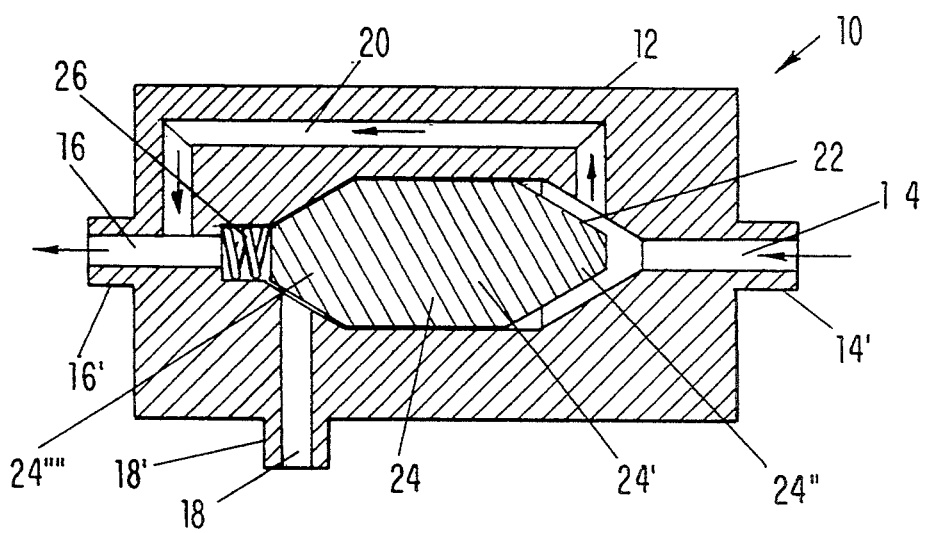
FIG. 1 is a cross-section of the preferred embodiment of the invention with hydraulic pressure applied.
Figure 2:
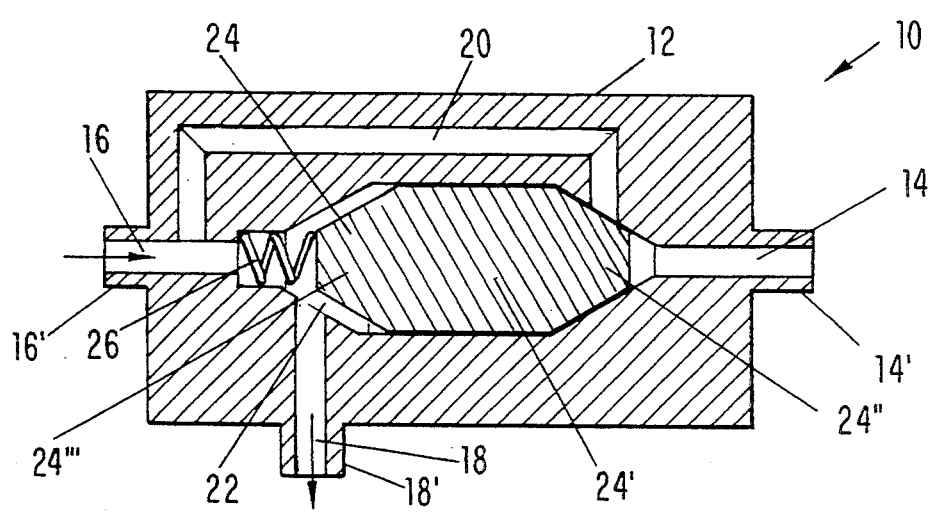
FIG. 2 is a cross-section of the preferred embodiment of the invention with mechanical force applied.

Reference is now made to FIGS. 1 and 2 which show the preferred embodiment of the invention. Lavage valve 10 comprises valve body 12. Valve body 12 further comprises first, second and third orifices 14, 16 and 18, as well as orifice extensions 14', 16', and 18', respectively. Valve body 12 further comprises bypass passageway 20 which bypasses central cavity 22 and interconnects orifices 14 and 16.

Valve member 24 is positioned within central cavity 22, complementary in configuration to valve member 24 for linear movement therein. Valve member 24 comprises cylindrical center portion 24' and truncated cone end portions 24" and 24''', respectively. End portions 24" and 24''' seat within orifices 14 and 16, respectively, of valve body 12, thereby occluding such orifices. Further, when valve member 24 is in position to occlude orifice 14, bypass passageway 20 is also occluded by end portion 24", as depicted in FIG. 2.

Orifice 18 (and orifice extension 18') are coupled to a vacuum source and receptacle or sump (not shown). As will be detailed later, the vacuum source sucks the irrigating fluid out of the patient, after completion of the procedure, and into the receptacle.

Valve 10 may comprise any suitable material compatible with its contemplated medical use. Accordingly, valve 10 may comprise any suitable plastic, stainless steel, aluminum and other such materials known to those ordinarily skilled in the art.

Typically, orifice extension 16' is coupled to a hypodermic needle or trocar and cannula for injecting irrigating or laving, fluid into and around the affected body parts of the patient. Orifice extension 14' is similarly coupled to a syringe barrel or the like initially containing the irrigating fluid, while orifice extension 18' is coupled to a vacuum source and receptacle (not shown).

The preferred couplings comprise the well known International Standard Luer conical male or female couplings In such case, orifice extension 14', 16' and 18' will comprise a 6° taper, and may also comprise the well known "Luer-Loks TM" coupling. Other couplings well known in the art may be employed.

The preferred embodiment of the invention further comprises biasing means such as, a helical or coil spring 26 positioned between end portion 24''' of valve member 24 and valve body 12. Spring 26 normally forces valve member 24 to the right as shown in FIG. 2, thereby occluding and sealing orifice 14 and bypass passageway 20. In normal operation, a hypodermic syringe or trocar is coupled to orifice extension 16', while a syringe barrel charged with irrigating fluid is coupled to orifice extension 14'. After insertion of the needle into the patient proximate the body part to be washed, the irrigating fluid is injected through orifice 14. The hydraulic pressure exerted by injection of the irrigating fluid overcomes the bias of spring 26, compressing spring 26, and moving valve member 24 to the left, as shown in FIG. 1. The entrance to bypass passageway 20 is opened allowing fluid to flow therethrough, as well as through orifice 16, to the body part to be washed. Flow continues until the irrigating fluid is totally injected or the hydraulic pressure exerted falls below the force required to compress spring 26. At such point, biasing spring 26 moves valve member 24 to the right, as shown in FIG. 2.

Such movement of valve member 24 to the right again (see FIG. 2) occludes orifice 14 and bypass passageway 20. Concomitantly, orifice 18 is opened, thereby permitting vacuum-induced flow of irrigating fluid out of the body into an appropriate receptacle or sump.

The lavage operation may be repeated as often as required by merely refilling the attached syringe barrel or replacing the empty syringe with a charged syringe. No manual manipulation of the valve itself is required, and leakage will not occur. Nevertheless, in order to ensure against reverse flow through orifice 18, a check valve (not shown) may be positioned therein. Such check valve would only permit flow of fluid to the receptacle and would preclude flow from the receptacle. Those ordinarily skilled in the art recognize that a simple ball, flap or cylinder-type check valve could be used, as well as any other check valve known to the art.

Figure 3:
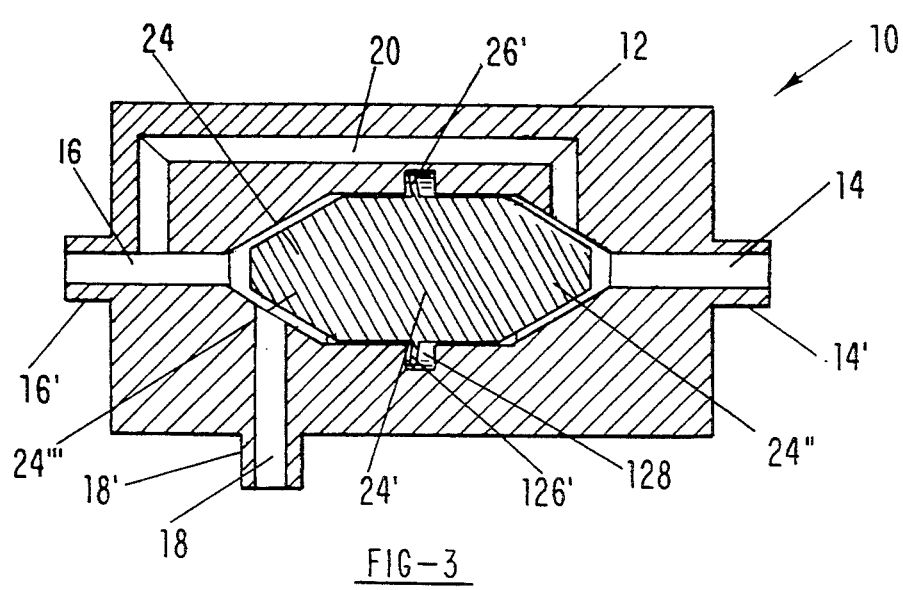
FIG. 3 is a cross-section of another embodiment of the invention.

FIG. 3 shows another embodiment of the invention. The FIG. 3 embodiment is otherwise identical in structure and operation to the preferred embodiment of FIGS. 1 and 2 and components are identically numbered. FIG. 3 illustrates the provision of annular projection 26' as a biasing spring. Projection 26' is centrally mounted and attached to valve member Projection 26' resembles a Belleville washer-type spring in function and configuration, and is lodged within annular recess 28 of valve body 12 for coaction therewith. As in the preferred embodiment of the invention of FIGS. 1 and 2, annular spring 26' normally biases valve member 24 into occlusion and sealing engagement with orifice 14.

The advantage of biasing spring 26' of the FIG. 3 embodiment over the spring employed in the FIGS. 1 and 2 embodiment is that annular spring 26' inherently prevents fluid passage around it by virtue of its configuration. On the other hand, use of annular spring 26' also entails possible reduced cycle life of the valve assembly.

Figure 4:
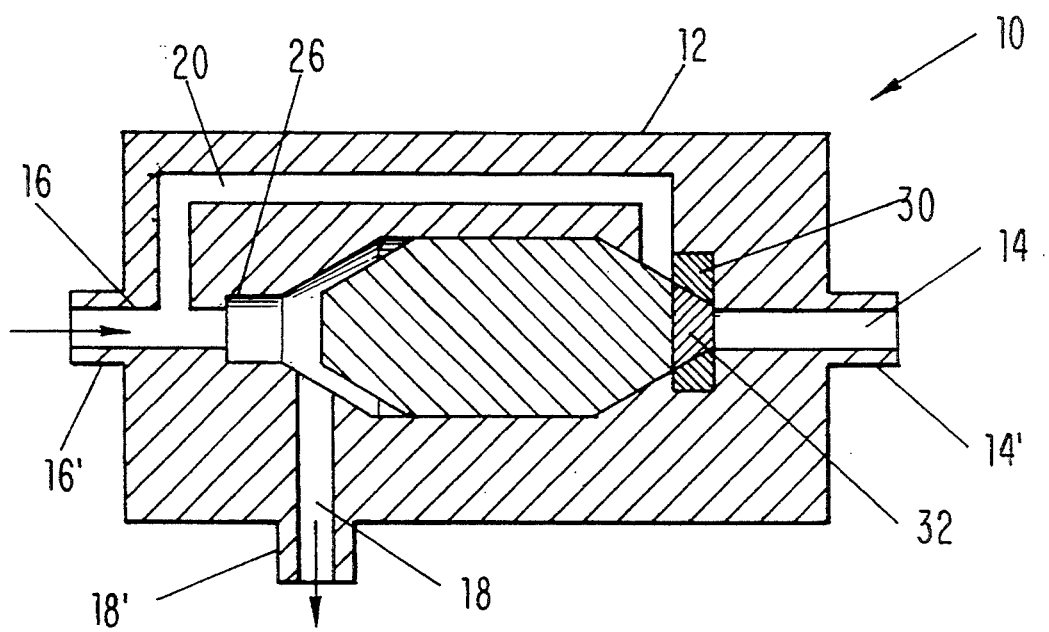
FIG. 4 is a cross-section of yet another embodiment of the invention.

FIG. 4 illustrates yet another embodiment of the invention. The FIG. 4 lavage valve embodiment utilizes magnetic biasing to occlude orifice 14. As illustrated, annular permanent magnet 30 attracts magnetic slug 32 resulting in occlusion of orifice 14. Those ordinarily skilled in the art will recognize that the relative positions of magnet 30 and magnetic slug 32 may be reversed with slug 32 on valve body 12 and magnet 30 on valve member 24, and, additionally, that magnetic slug 32 may also be polarized (with unlike poles adjacent to poles of magnet 30). In order to avoid magnetic stiction, both magnet 30 and slug 32 should have nonmagnetic layering, such as plastic or stainless steel valve material or other material such as Stellite TM, brass or the like, well known to those skilled in the art. Operation of the FIG. 4 embodiment otherwise is similar to the FIGS. 1 and 2 preferred embodiment: Permanent magnet 30 and magnetic slug 32 bias valve member 24 into sealing engagement with orifice 14, thereby occluding orifice 14, until such bias is overcome by hydraulic pressure from an attached syringe barrel.

Figure 5:
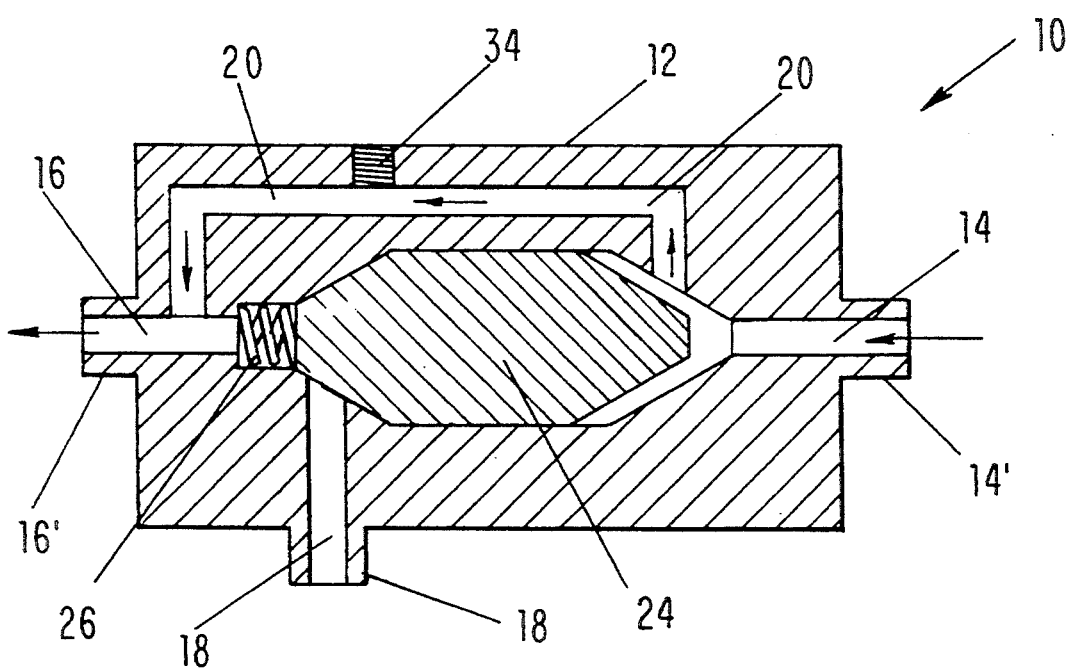
FIG. 5 is a cross-section of still another embodiment of the invention.

Still another embodiment of the invention is depicted in FIG. 5. The FIG. 5 embodiment comprises threaded aperture 34 in valve body 12. Threaded aperture 34 provides communication between bypass passageway 20 and the ambient atmosphere, and primarily serves as a training or monitoring device.

Figure 6:
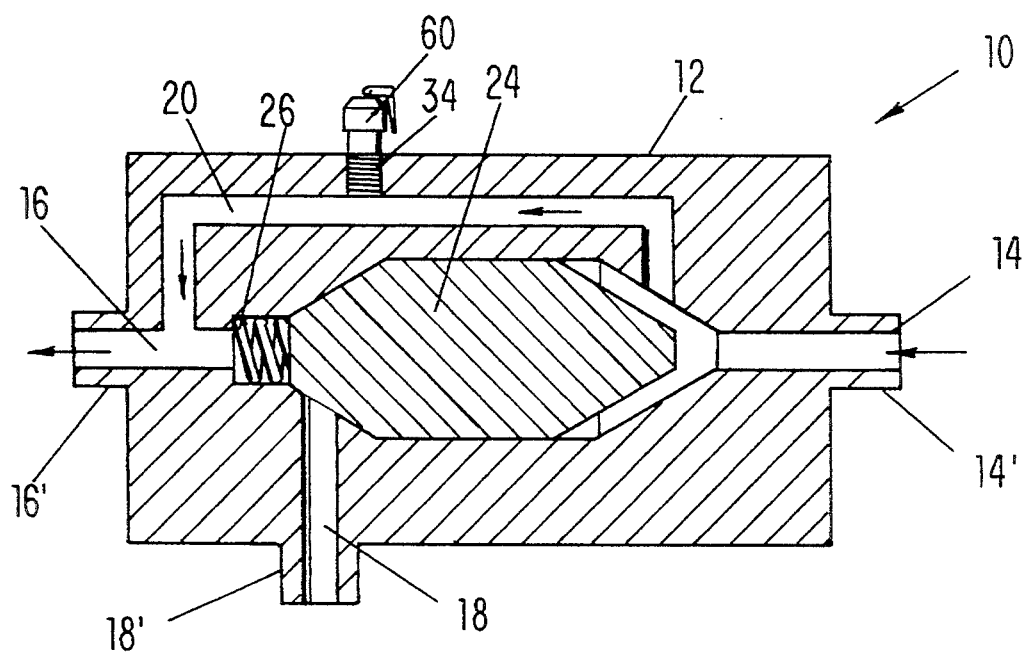
FIG. 6 is a perspective view of a pressure relief valve usable in combination with the FIG. 5 embodiment.

FIG. 6 depicts a threaded attachment 60 used in combination with aperture 34. Attachment 60 comprises a "pop off" or pressure relief valve with stem adapted to be screwed or otherwise secured into aperture 34. Pressure relief valve 60 is set to open at a predetermined pressure, for example 21 mm Hg or 20 cm H₂O. In operation, medical personnel manually applying pressure to the irrigating syringe would thus be encouraged to apply steady, constant pressure (less than a predetermined pressure) to the irrigating syringe; exceeding the predetermined pressure would open the valve and vent the irrigating fluid.

Figure 7:
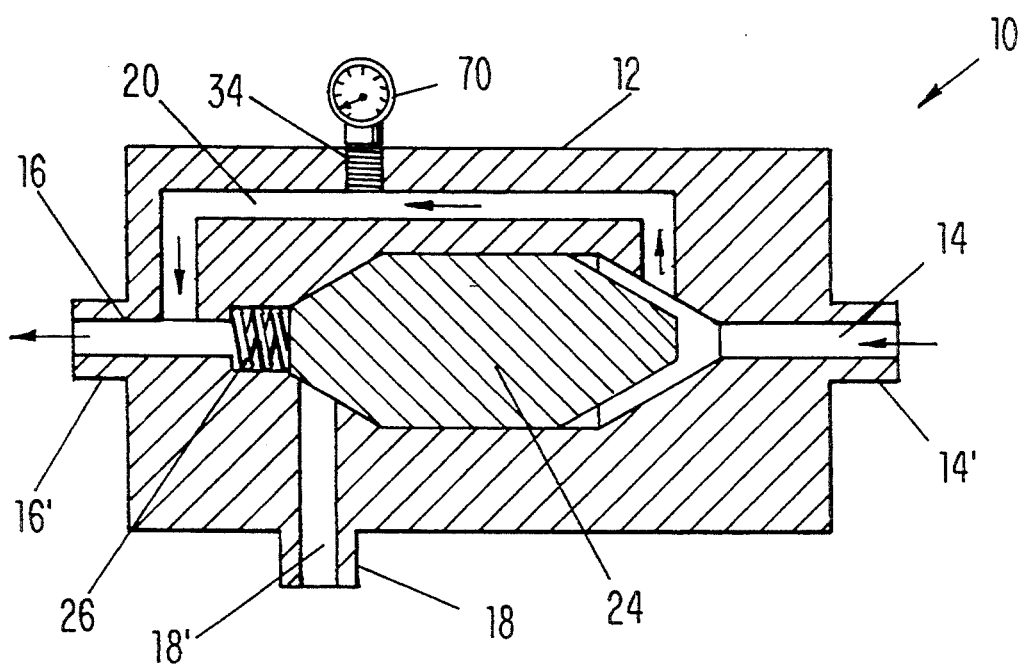
FIG. 7 is a perspective view of a pressure gauge usable in combination with the FIG. 5 embodiment.

Similarly, attachment 70 shown in FIG. 7 also serves as a training or monitoring aid. Attachment 70 is a pressure gauge with stem; gauge 70 screws or is otherwise secured into aperture 34, thus affording a visual indication of actual pressure applied to the irrigating syringe. Such visual indication of pressure applied would also tend to encourage steady, uniform application of manual pressure upon the irrigating syringe.

Those skilled in the art will recognize that any known means of securement or attachment may be used to secure valve 60 and gauge 70 in valve body 12, including the threaded means depicted.

The lavage valve of the present invention is useful whenever irrigation of an organ, joint or cavity is required, e.g. attachment to bronchoalveolar lavage catheters, for irrigating the urinary bladder, thoracic cavity, gastric cavity, joints, abscesses, cavities and other infected or fluidized body spaces.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. Valve apparatus comprising:
    a valve body comprising first, second and third orifices and a bypass passageway; a valve member comprising first and second end portions and movable within said valve body; means for biasing said valve member; and
    means for applying pressure to said first end portion, thereby opening said first orifice and said bypass passageway while occluding said third orifice;
    wherein said means for biasing said valve member comprises means for biasing said valve member into occluding said first orifice and said bypass passageway while opening said second and third orifices.

2. The invention of claim 1 wherein said valve member comprises cylindrical center portion means.

3. The invention of claim 1 wherein said first and second end portions comprise first and second truncated cone end portions.

4. The invention of claim 1 wherein said valve body comprises a hollow central portion complementary in configuration to said valve member.

5. The invention of claim 1 wherein said biasing means comprises helical spring means.

6. The invention of claim 1 wherein said biasing means comprises annular spring means.

7. The invention of claim 1 wherein said biasing means comprises magnetic means.

8. The invention of claim 1 wherein said means for applying pressure comprises means for applying hydraulic pressure, thereby directing fluid flow through said first and second orifices and said bypass passageway.

9. The invention of claim 1 wherein said bypass passageway comprises an aperture.

10. The invention of claim 9 further comprising pressure relief valve disposed in said aperture.

11. The invention of claim 9 further comprising a pressure gauge disposed in said aperture.

12. A method for using a valve comprising the steps of:
    providing a valve body comprising first, second and third orifices and bypass passageway;
    providing a valve member comprising first and second end portions, and movable in the valve body;
    biasing the valve member; and
    applying pressure to the first end portion thereby opening the first orifice and bypass passageway and occluding the second and third orifices;
    wherein the step of biasing the valve member comprises the steps of occluding the first orifice and bypass passageway while opening the second and third orifices.

13. The method of claim 12 wherein the step of applying pressure further comprises the step of applying hydraulic pressure and thereby directing fluid flow through the first and second orifices and the bypass passageway.

* * * * *